United States Patent
Pradhan et al.

(10) Patent No.: US 11,773,112 B2
(45) Date of Patent: Oct. 3, 2023

(54) SYNTHESIS OF TETRAZOLATE SALTS

(71) Applicant: PRIMODIA CHEMICALS AND PHARMACEUTICALS PRIVATE LIMITED, Telangana (IN)

(72) Inventors: Braja Sundar Pradhan, Udumulapadu (IN); Sanjeev K. Singh, Picatinny Arsenal, NJ (US); Neha H. Mehta, Picatinny Arsenal, NJ (US)

(73) Assignee: PRIMODIA CHEMICALS AND PHARMACEUTICALS PRIVATE LIMITED, Hyderabad (IN)

( * ) Notice: Subject to any disclaimer, the term of this patent is extended or adjusted under 35 U.S.C. 154(b) by 14 days.

(21) Appl. No.: 17/542,235

(22) Filed: Dec. 3, 2021

(65) Prior Publication Data

US 2022/0177493 A1 Jun. 9, 2022

(30) Foreign Application Priority Data

Dec. 5, 2020 (IN) .............................. 202041053023

(51) Int. Cl.
*C07F 1/00* (2006.01)
*C07F 1/08* (2006.01)
*C07D 257/06* (2006.01)

(52) U.S. Cl.
CPC .............. *C07F 1/08* (2013.01); *C07D 257/06* (2013.01)

(58) Field of Classification Search
CPC ................................. C07F 1/08; C07D 257/06
USPC .......................................... 548/101, 107, 251
See application file for complete search history.

(56) References Cited

U.S. PATENT DOCUMENTS 9,440,934 B1 * 9/2016 Mehta .................. C07D 257/06

* cited by examiner

*Primary Examiner* — Charanjit Aulakh
(74) *Attorney, Agent, or Firm* — Maschoff Brennan

(57) ABSTRACT

The present invention relates to a novel method of synthesis of copper (I) 5-nitrotetrazolate. Particularly, for the synthesis of the copper (I) 5-nitrotetrazolate, the present invention uses a suitable salt of 5-aminotetrazole, preferably the sulfate or the nitrate salt as the starting compound. The selection of the said starting chemical not only eliminates any safety issue arising during Sandmeyer reaction conditions to affect the functional group conversion but also greatly improves the ease of executing the synthetic protocol, rendering the process safe to be adopted for commercial manufacture of the copper (I) 5-nitrotetrazolate compound.

8 Claims, No Drawings

SYNTHESIS OF TETRAZOLATE SALTS

FIELD OF THE INVENTION

The invention disclosed herein relates to the field of tetrazole chemistry, in particular, it outlines a methodology for the synthesis of various tetrazolate salts, including 5-nitrotetrazolate salts. More importantly, the invention can be safely adopted for commercial manufacture of all types of tetrazolate compounds, including copper (I) 5-nitrotetrazolate.

BACKGROUND OF THE INVENTION

5-Nitrotetrazolate salts have industrial applications in mining and construction industries, as a 5-nitrotetrazolate derivative is appropriately qualified to replace lead azide, a toxic and environmentally polluting compound used in the mentioned industries. The current methods of preparation of 5-nitrotetrazolate compounds, particularly, copper (I) 5-nitrotetrazolate, comprises of two steps. In the first reaction step, 5-nitrotetrazole is prepared from 5-aminotetrazole under Sandmeyer reaction conditions and thereafter in the second step, its sodium salt is coupled with cuprous chloride (CuCl) or with a cupric salt and a reductant.

These processes, however, are plagued with serious drawbacks such as tedious work up conditions to isolate the product from aqueous reaction mixture and serious safety issues during the preparation of the intermediate 5-nitrotetrazole under Sandmeyer reaction conditions. These issues render the existing processes utterly unsafe and unsuitable to be adopted for industrial manufacture of copper (I) 5-nitrotetrazolate.

One aspect of the invention disclosed herein pertains to finding a practical solution to the above-mentioned drawbacks inherently present in current methods of preparation of copper (I) 5-nitrotetrazolate. The problem was solved by replacing the starting chemical, namely, 5-aminotetrazole, with one of its salts, preferably, a sulfate, or a nitrate salt of 5-aminotetrazole. The selection of such a salt of 5-aminotetrazole as the starting material completely eliminates safety issues that are encountered during the functional group conversion involving Sandmeyer reaction.

The other aspect of the disclosed invention herein pertains to the ease of executing the synthesis of the copper (I) 5-nitrotetrazolate on a commercial scale. The chemistry inherent in the disclosed invention completely eliminates tedious operations of the current processes involving multiple filtrations, washings and careful execution of isolation techniques to retrieve the finished product from the aqueous mixture.

SUMMARY OF THE INVENTION

The present invention discloses a novel method of preparation of copper (I) 5-nitrotetrazolate. Particularly, for the synthesis of the copper (I) 5-nitrotetrazolate, the present invention uses a suitable salt of 5-aminotetrazole, preferably the sulfate or the nitrate salt as the starting chemical compound. The selection of the said starting compound not only eliminates safety issues arising during Sandmeyer reaction conditions to affect the functional group conversion but also greatly improves the ease of executing the synthetic protocol, rendering the process safe to be adopted for commercial manufacture of the copper (I) 5-nitrotetrazolate compound.

In a particular embodiment, the present invention relates to a method of synthesis of copper (I) 5-nitrotetrazolate, wherein the method comprises (a) using a salt of 5-aminotetrazole as a starting compound for the synthesis of the copper (I) 5-nitrotetrazolate, (b) adding an acid to an aqueous mixture comprising of (i) the salt of 5-aminotetrazole, (ii) sodium nitrite ($NaNO_2$) and (iii) a copper salt or its hydrated form, at a suitable temperature to form a reaction mixture, (c) stirring and heating the reaction mixture to form 5-nitrotetrazole in situ, (d) adding an aqueous solution of sodium hydroxide (NaOH) to the reaction mixture at a particular temperature to convert 5-nitrotetrazole formed in step (c) to its sodium salt in situ, and a precipitated dark compound, (e) filtering off the precipitated dark compound in step (d) to obtain a filtrate containing the said sodium salt of 5-nitrotetrazole, (f) heating the filtrate containing the sodium salt of 5-nitrotetrazole at a particular temperature followed by addition of cuprous chloride(CuCl) to the filtrate until a colored solid is precipitated out of the reaction mixture, and (g) filtering the precipitated colored solid after removing all impurities, washing the precipitated solid successively with hot water and alcohol, and drying the precipitated colored solid to obtain the copper (I) 5-nitrotetrazolate.

In an embodiment, the salt of 5-aminotetrazole is preferably a nitrate or a sulphate salt of 5-aminotetrazole. In another embodiment, the acid added to the aqueous mixture is one of nitric acid ($HNO_3$), preferably 65% nitric acid ($HNO_3$). In yet another embodiment, the acid is added to the aqueous mixture at a temperature of 5 to 20° C. In a particular embodiment, the copper salt or its hydrated form is one of copper (II) sulphate or copper (II) sulfate pentahydrate.

In an embodiment, the reaction mixture is stirred at 10 to 15° C. temperature for 10 minutes to 3 hours, and then the reaction mixture is heated to 100° C. and maintained at this temperature until the reaction is complete, resulting in the formation of 5-nitrotetrazole in situ. In another embodiment, the aqueous solution of sodium hydroxide (NaOH) is added to the reaction mixture comprising the 5-nitrotetrazole at a temperature ranging from 60° C. to 100° C. until the pH of the reaction mixture is turned basic. In a particular embodiment, the filtrate containing the sodium salt of 5-nitrotetrazole is heated to 100° C. —at which stage copper (I) chloride is added, and the mixture is thereafter maintained at this temperature until the precipitation of the colored solid is complete.

In an embodiment, the copper (II) cations present in the aqueous solution are converted in situ to copper (I) cations by a suitable reductant, namely sodium bisulfite. The copper (I) cations thus generated can be used in situ to prepare copper (I) 5-nitrotetrazolate, thereby avoiding the filtration step and optimizing the use of copper (II) salt in the process.

DETAILED DESCRIPTION OF THE INVENTION

It should be noted that the detailed description and examples merely illustrate the principles of the present subject matter. It should be appreciated by those skilled in the art that conception and specific embodiments disclosed may be readily utilized as a basis for modifying or designing other methods for carrying out the same purposes of the present subject matter. Furthermore, all examples recited herein are principally intended expressly to be for pedagogical purposes to aid the reader in understanding the principles of the present subject matter and the concepts contributed by the inventor(s) to furthering the art and are to be construed as being without limitation to such specifically recited examples and conditions. The novel features which are believed to be characteristic of the present subject matter, both as to its organization and method of operation, together with further objects and advantages will be better understood from the following description when considered in connection with the accompanying examples.

These and other advantages of the present subject matter would be described in greater detail with reference to the following examples. It should be noted that the description merely illustrates the principles of the present subject matter. It will thus be appreciated that those skilled in the art will be able to devise various arrangements that, although not explicitly described herein, embody the principles of the present subject matter and are included within its scope.

In a preferred embodiment, the method of synthesis of copper (I) 5-nitrotetrazolate comprises commencing with the preparation of a sodium salt of 5-nitrotetrazole, which is also the penultimate intermediate of copper (I) 5-nitrotetrazolate. The reason and advantage for commencing the synthesis with the preparation of the sodium salt of 5-nitrotetrazole using a salt of 5-aminotetrazole is that not only it eliminates safety issues arising during Sandmeyer reaction conditions but it also greatly improves the ease of executing the synthetic protocol, rendering the process safe and viable to be adopted for commercial manufacture of the copper (I) 5-nitrotetrazolate compound.

In an embodiment, the method comprises subjecting, a suitable salt of 5-aminotetrazole, preferably the nitrate salt, to Sandmeyer reaction conditions whereby, an acid, preferably nitric acid ($HNO_3$), is added to an aqueous mixture comprising of (i) a sulfate or a nitrate salt, preferably, the nitrate salt of 5-aminotetrazole, (ii) sodium nitrite ($NaNO_2$) and (iii) a copper salt or its hydrated form, preferably the hydrated form of copper sulfate at 5 to 20° C. In an embodiment, the copper salt or its hydrated form is one of copper (II) sulphate or copper (II) sulfate pentahydrate. In an embodiment, following the addition of the dilute nitric acid ($HNO_3$) to the aqueous mixture, the reaction mixture is stirred at 10 to 15° C. temperature for 10 minutes to 3 hours, and is then heated to 100° C. The mixture is thereafter maintained at this temperature until the reaction is complete. This method of executing Sandmeyer reaction conditions results in a clean functional group conversion without concomitant triggering of any safety issue. The 5-nitrotetrazole thus formed in situ is not isolated from the mixture, and is thereafter converted to its sodium salt in situ. Accordingly, in this way, the sodium salt of 5-nitrotetrazole is prepared safely for further synthesis and conversion to the copper (I) 5-nitrotetrazolate compound.

In an embodiment, for the conversion of the 5-nitrotetrazole in situ to its sodium salt, the method comprises of adding an aqueous solution of sodium hydroxide (NaOH) to the reaction mixture at a temperature ranging from 60° C. to 100° C. until the pH of the reaction mixture is turned basic. The addition of sodium hydroxide (NaOH) results in the formation of the sodium salt of 5-nitrotetrazole that remains in the aqueous mixture, but forces the precipitation of a dark solid compound. The precipitated dark solid compound is then filtered off at room temperature. The filtrate containing the sodium salt of 5-nitrotetrazole is thereafter heated to 100° C. followed by the addition of an aqueous suspension of cuprous chloride (CuCl) or solid cuprous chloride to the filtrate. The mixture is maintained at this temperature until the precipitation of a colored solid is complete. The precipitated colored solid is thereafter filtered after carefully removing all impurities, washed successively with hot water and isopropyl alcohol and dried to give the desired copper (I) 5-nitrotetrazolate as a colored solid in good yield.

WORKING EXAMPLE: 1

An aqueous solution of a mixture of the nitrate salt of 5-aminotetrazole (25 g) and a catalytic amount of copper sulfate pentahydrate was added drop by drop to an aqueous solution of copper sulfate pentahydrate (41 g) and sodium nitrite ($NaNO_2$) (35 g) at 10° C. Following the addition, the mixture was stirred at this temperature for 1 hour. A dilute nitric acid ($HNO_3$) (22.5 ml) was then added to the mixture drop by drop at this temperature. The mixture was allowed to warm to room temperature, heated to 100° C. and maintained at this temperature until the functional group conversion was complete. Following the completion of the reaction, the mixture was allowed to cool down to 70° C. when an aqueous solution of sodium hydroxide (NaOH) was added to the mixture drop by drop until the pH of the mixture remained within the range 7-9.5. The mixture was stirred for 1 hour at this temperature while maintaining the pH within the mentioned range. The mixture was then allowed to cool down to room temperature. The precipitated dark solid was filtered off. The filtrate was heated to 100° C. and cuprous chloride (CuCl) (10 g) was added at this temperature. The mixture was stirred at this temperature until the precipitation of copper (I) 5-nitrotetrazolate was complete. The colored precipitate was filtered after removing all the insoluble impurities, washed successively with hot water, isopropyl alcohol and air dried to give the required product as a deep maroon colored solid with an efficient yield of 11-12 g.

WORKING EXAMPLE 2

An aqueous solution of a mixture of the nitrate salt of 5-aminotetrazole (25 g, 168.83 mmole) and copper sulfate pentahydrate (4 g, 16.02 mmole) was added drop-by-drop to an aqueous solution of a mixture of sodium nitrite ($NaNO_2$) (35 g, 507.28 mmole) and copper sulfate pentahydrate (41.7 g, 167.01 mmole) over a period of 30 minutes at 18° C. Following the addition, nitric acid ($HNO_3$) (65%, 22.5 ml) was added drop-by-drop to the mixture over a period of 30 minutes at this temperature. The mixture was heated to 100° C., and maintained at this temperature for 10 minutes until the functional group conversion was complete. The mixture was allowed to cool down to 70° C. An aqueous solution of sodium hydroxide (NaOH) was added drop-by-drop to the mixture at this temperature until the pH of the mixture turned basic. After the completion of the addition, the mixture was stirred at this temperature for 2 h, and then allowed to cool down to room temperature. The precipitated colored material was filtered off and the filtrate was heated to 100° C. Copper (I) chloride (10 g, 101 mmole) was added to the mixture. After 2 h at this temperature, the precipitated red colored solid was isolated from the mixture after removing all the impurities, washed successively with hot water and isopropyl alcohol and dried to give copper (I) 5-nitrotetrazolate with an efficient yield of 11-12 g.

In another embodiment, the copper (II) cations present in the aqueous solution are converted in situ to copper (I) cations by a suitable reductant such as sodium bisulfite. The conversion of copper (II) cations present in the reaction to copper (I) cations in situ, led to an improved process of preparation of copper (1) 5-nitrotetrazolate. The improved process avoids the filtration step and optimizes the use of copper (II) sulfate in the reaction.

In an embodiment, 5-nitrotetrazole was treated in situ with an aqueous solution of a mixture comprising of sodium salts, namely, sodium hydroxide (NaOH), sodium bisulfite, and sodium chloride. The aqueous solution was added drop-by-drop to the reaction mixture at 60° C. to 100° C. Following the addition, the mixture was maintained at 100° C. until the copper (I) 5-nitrotetrazolate is precipitated completely out of the aqueous mixture.

The terms "comprises", "comprising", or any other variations thereof used in the disclosure, are intended to cover a non-exclusive inclusion, such that a method that comprises a list of steps does not include only those method steps but may include other steps not expressly listed or inherent to such method. In other words, one or more steps in a method proceeded by the expression "comprises . . . a" does not, without more constraints, preclude the existence of other steps or additional steps in the method.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

It will be further appreciated that functions of a plurality of steps may be combined into a single step, or the functions of one-step may be split among plural steps. The present invention contemplates all of these combinations. In addition, while a feature of the present invention may have been described in the context of only one of the illustrated embodiments, such feature may be combined with one or more other features of other embodiments, for any given application. The present invention also encompasses intermediate and end products resulting from the practice of the methods herein. The use of "comprising" or "including" also contemplates embodiments that "consist essentially of" or "consist of" the recited feature.

Although embodiments for the present subject matter have been described in a language specific to process features, it is to be understood that the present subject matter is not necessarily limited to the specific features described herein. Rather, the specific features and methods are disclosed as embodiments for the present subject matter. Numerous modifications and adaptations of the method of the present invention will be apparent to those skilled in the art, and thus it is intended by the appended description to cover all such modifications and adaptations which fall within the scope of the present subject matter.

We claim:

1. A method of synthesis of copper (I) 5-nitrotetrazolate, the method comprises:
    a) using a nitrate salt of 5-aminotetrazole as a starting compound for the synthesis of the copper (I) 5-nitrotetrazolate;
    b) adding an acid to an aqueous mixture comprising of (i) the nitrate salt of 5-aminotetrazole, (ii) sodium nitrite (NaNO$_2$) and (iii) a copper salt or its hydrated form, at a suitable temperature to form a reaction mixture;
    c) stirring and heating the reaction mixture to form 5-nitrotetrazole in situ;
    d) adding an aqueous solution of sodium hydroxide (NaOH) to the reaction mixture at a particular temperature to convert 5-nitrotetrazole formed in step (c) to its sodium salt in situ, and a precipitated dark compound;
    e) filtering off the precipitated dark compound formed in step (d) to obtain a filtrate containing the said sodium salt of 5-nitrotetrazole;
    heating the filtrate containing the sodium salt of 5-nitrotetrazole to a particular temperature followed by addition of cuprous chloride (CuCl) to the filtrate until a colored solid is precipitated out of the reaction mixture;
    filtering the precipitated colored solid after removing all impurities, washing the precipitated solid successively with hot water and alcohol, and drying the precipitated colored solid to obtain the copper (I) 5-nitrotetrazolate.

2. The method as claimed in claim 1, wherein the acid added to the aqueous mixture is nitric acid (HNO$_3$), preferably 65% nitric acid (HNO$_3$).

3. The method as claimed in claim 1, wherein the acid is added to the aqueous mixture at a temperature range of 5 to 20° C.

4. The method as claimed in claim 1, wherein the copper salt or its hydrated form is one of copper (II) sulphate or copper (II) sulfate pentahydrate.

5. The method as claimed in claim 1, wherein the reaction mixture is stirred at 10 to 15° C. temperature for 10 minutes to 3 hours, and then the reaction mixture is heated to 100° C. and maintained at this temperature until the reaction is complete, resulting in the formation of 5-nitrotetrazole in situ.

6. The method as claimed in claim 1, therein the aqueous solution of sodium hydroxide (NaOH) is added to the reaction mixture comprising 5-nitrotetrazole at a temperature ranging from 60° C. until the pH of the reaction mixture is turned basic.

7. The method as claimed in claim 1, wherein the filtrate containing the sodium salt of 5-nitrotetrazole is heated to 100° C., followed by the addition of copper (I) chloride and is maintained at this temperature until the precipitation of a colored solid is complete.

8. The method as claimed in claim 1, wherein the copper (II) cations present in the aqueous solution are converted in situ to copper (I) cations by a suitable reductant, namely sodium bisulfite.

* * * * *